United States Patent
Lee et al.

(10) Patent No.: US 12,062,190 B2
(45) Date of Patent: Aug. 13, 2024

(54) APPARATUS AND METHOD FOR MEASURING EYE MOVEMENT

(71) Applicant: INDUSTRY-ACADEMIC COOPERATION FOUNDATION, YONSEI UNIVERSITY, Seoul (KR)

(72) Inventors: Seung Ah Lee, Seoul (KR); Tae Young Kim, Seoul (KR); Kyung Won Lee, Seoul (KR); Nak Kyu Baek, Seoul (KR); Jae Woo Jung, Seoul (KR)

(73) Assignee: INDUSTRY-ACADEMIC COOPERATION FOUNDATION, YONSEI UNIVERSITY, Seoul (KR)

( * ) Notice: Subject to any disclaimer, the term of this patent is extended or adjusted under 35 U.S.C. 154(b) by 0 days.

(21) Appl. No.: 18/052,192

(22) Filed: Nov. 2, 2022

(65) Prior Publication Data

US 2024/0153104 A1   May 9, 2024

(30) Foreign Application Priority Data

Nov. 5, 2021 (KR) .................. 10-2021-0151048

(51) Int. Cl.
| | |
|---|---|
| *G06T 7/246* | (2017.01) |
| *A61B 5/00* | (2006.01) |
| *A61B 5/16* | (2006.01) |
| *G06T 7/00* | (2017.01) |
| *G06T 7/73* | (2017.01) |
| *H04N 23/56* | (2023.01) |
| *H04N 25/531* | (2023.01) |
| *A61B 3/14* | (2006.01) |

(52) U.S. Cl.
CPC ............ *G06T 7/246* (2017.01); *A61B 5/163* (2017.08); *A61B 5/4088* (2013.01); *A61B 5/7246* (2013.01); *G06T 7/0012* (2013.01); *G06T 7/73* (2017.01); *H04N 23/56* (2023.01); *H04N 25/531* (2023.01); *A61B 3/14* (2013.01); *G06T 2207/30041* (2013.01)

(58) Field of Classification Search
CPC ......... G06T 7/246; G06T 7/73; G06T 7/0012; G06T 2207/30041; A61B 5/163; A61B 5/4088; A61B 5/7246; A61B 3/14; H04N 25/531; H04N 23/56
USPC ........................................................ 348/78
See application file for complete search history.

(56) References Cited

U.S. PATENT DOCUMENTS

| | | | | |
|---|---|---|---|---|
| 2005/0194514 | A1* | 9/2005 | Izumi ................. | G02B 6/29358 250/201.9 |
| 2007/0036429 | A1* | 2/2007 | Terakawa ............ | G06V 40/165 382/118 |
| 2017/0285738 | A1* | 10/2017 | Khalid ................... | G06T 15/20 |
| 2021/0166341 | A1* | 6/2021 | Bastani .................. | G06T 11/00 |

FOREIGN PATENT DOCUMENTS

| | | |
|---|---|---|
| JP | 2014-217756 A | 11/2014 |
| KR | 10-2016-0126060 A | 11/2016 |
| KR | 10-1711093 B1 | 3/2017 |

* cited by examiner

*Primary Examiner* — Allen C Wong

(57) ABSTRACT

The disclosed embodiment provides an apparatus and method for measuring eye movement, that can accurately measure eye movement by determining the eye position at high speed and high resolution even with a low-cost camera by using a phase mask and rolling shutter method instead of a lens, and can perform early diagnosis of neurological diseases, etc. based on the measured eye movement.

17 Claims, 9 Drawing Sheets

APPARATUS AND METHOD FOR MEASURING EYE MOVEMENT

CROSS-REFERENCE TO RELATED APPLICATIONS

This application claims priority under 35 U.S.C. § 119(a) to Korean Patent Application No. 10-2021-0151048, filed on Nov. 5, 2021, with the Korean Intellectual Property Office, the disclosure of which is incorporated herein in its entirety by reference.

BACKGROUND

1. Technical Field

The present disclosure relates to an apparatus and method for measuring eye movement, and more particularly to an apparatus and method for measuring eye movement for early detection of a degenerative neuronal disease.

2. Description of the Related Art

Eye movement measurement, or eye tracking, is used in a variety of fields, from VR/AR, psychology, marketing to medical purposes. However, the performance required for each application field is different.

Among the fields where eye tracking is used, in the medical field, eye tracking technology is applied as a method of diagnosing diseases based on eye movement. Recently, in the medical field, the possibility has emerged that the frequency and intensity of micro-saccades that occur when the eyes look at a fixed object are neurologically related to dementia, and thus can be used to diagnose neurological diseases such as dementia or Parkinson's disease. In other words, it was suggested that early detection of degenerative neuronal diseases can be made by measuring eye movement. However, when measuring eye movement to accurately diagnose neurological diseases in the medical field, high-speed, high-resolution eye tracking technology is required.

Three methods are generally used for eye tracking: a method of attaching a special lens or the like to the eye, a method of measuring and analyzing the electrical potential according to eye movement, and a method of capturing and analyzing a video or image. Among these, in the case of special lenses or methods of measuring electrical potential, equipment that is attached directly to the eye is used, making it complicated to use and expensive, making it difficult to access, so image-based eye tracking techniques with relatively simple structures are mainly used.

Image-based eye tracking mainly consists of a method of tracking gaze based on the position of the center point by imaging the entire eye with a specific light source and calculating the position of the center point based on the shape of the circular or oval pupil, and a method of tracking gaze based on the position of the reflection (Purkinje reflection) point that appears when a light source reflects off the eye. The shape and position of the light source and camera vary depending on the optical system configuration of the system, and may be positioned to suit wearable devices such as head mounts, glasses, and goggles, or may be configured in a bar shape. A form that is relatively straight and fixable in alignment with the eye has the characteristics of being strong in resolution and noise.

However, the measurement speed of eye tracking based on video tracking is limited by the frame rate of the camera sensor. Currently, in the case of conventional eye trackers, it is generally difficult to measure micro-saccadic eye movement (fixational eye movement) with a size of 0.1 to 1°, a frequency of 2 Hz or less, and a speed of up to 300°/s. In other words, the temporal and spatial resolution of the camera is low, which limits its use for medical purposes.

Therefore, in order to use image-based eye tracking techniques for medical purposes, expensive cameras with high frame rates and high resolution must be used, or complex optical systems must be used, which increases costs and reduces usability.

SUMMARY

The disclosed embodiments are aimed at providing an apparatus and method for measuring eye movement that can accurately measure eye movement at high speed and high resolution.

The disclosed embodiments are aimed at providing an apparatus and method for measuring eye movement that can track gaze by determining the eye position at high speed and high resolution even with a low-cost camera using a phase mask and rolling shutter method instead of a lens.

An apparatus for measuring eye movement according to an embodiment comprises: a light source that emits light in the direction of an eye; a phase mask that phase-converts light reflected and incident from the eye according to a pre-formed phase shift pattern; an image sensor unit including a plurality of optical sensors that generate a plurality of detection signals by detecting light that is phase-converted by the phase mask and distributed and projected at different intensities for each position; a rolling image extraction unit that sequentially moves a window of a pre-designated size for the plurality of optical sensors according to a rolling shutter method and generates a partial image by receiving a detection signal generated at an optical sensor included in the window; a point spread function storage unit that pre-stores a point spread function corresponding to the phase shift pattern of the phase mask; a cross-correlation unit that cross-correlates the partial image and the point spread function to obtain a correlation value according to the position between the partial image and the point spread function; and an eye movement measurement unit that detects the peak of the correlation value, and tracks the position of light by determining and accumulating the angle at which light is incident based on the position between the partial image at the detected peak and the point spread function, thereby analyzing eye movement.

The phase mask may be implemented as a transparent film formed to have different heights at each position on one side according to the phase shift pattern.

The point spread function may be obtained in advance based on an image pattern generated by the light emitted from a light source at a pre-designated reference position being phase-converted through the phase mask and then projected onto the image sensor unit.

The point spread function may be obtained by background subtraction and sharpness filtering on the image pattern generated by the projection.

The window may be set to a size that can distinguish the plurality of optical sensors according to a ratio between a frame rate according to a time interval required for optical position tracking compared to a frame rate designated for the image sensor unit.

The cross-correlation unit may extract a partial point spread function of a size corresponding to the window at a position corresponding to the partial image from the point spread function, and cross-correlate the partial image and the extracted partial point spread function.

The cross-correlation unit may expand the outline of the partial point spread function by a pre-designated size, perform mean replacement padding on the expanded area, and then perform cross-correlation.

The eye movement measurement unit may detect the position where the peak occurs separately in the X-axis direction and the Y-axis direction, and accumulate peak positions detected in each of the X-axis and Y-axis directions, thereby tracking changes in the position of the light.

A method for measuring eye movement according to an embodiment comprises the steps of: emitting light in the direction of an eye; the light reflected and incident from the eye being phase-converted through a phase mask in which a pre-designated phase shift pattern is formed in advance, distributed and projected at different intensities for each position, an image sensor unit generating a plurality of detection signals by detecting the light with a plurality of optical sensors; generating a partial image by sequentially moving a window of a pre-designated size for the plurality of optical sensors according to a rolling shutter method and receiving a detection signal generated at an optical sensor included in the window; cross-correlating the partial image and a point spread function pre-stored corresponding to the phase shift pattern of the phase mask to obtain a correlation value according to the position between the partial image and the point spread function; and detecting the peak of the correlation value, tracking the position of light by determining and accumulating the angle at which light is incident based on the position between the partial image at the detected peak and the point spread function, thereby measuring eye movement.

Accordingly, according to the apparatus and method for measuring eye movement of the embodiment, eye movement can be accurately measured by determining the eye position at high speed and high resolution even with a low-cost camera by using a phase mask and rolling shutter method instead of a lens, and early diagnosis of neurological diseases, etc. can be performed based on the measured eye movement.

DETAILED DESCRIPTION OF THE INVENTION

Hereinafter, specific embodiments of an embodiment will be described with reference to the accompanying drawings. The following detailed description is provided to assist in a comprehensive understanding of the methods, devices and/or systems described herein. However, the detailed description is only for illustrative purposes and the present disclosure is not limited thereto.

In describing the embodiments, when it is determined that detailed descriptions of known technology related to the present disclosure may unnecessarily obscure the gist of the present disclosure, the detailed descriptions thereof will be omitted. The terms used below are defined in consideration of functions in the present disclosure, but may be changed depending on the customary practice or the intention of a user or operator. Thus, the definitions should be determined based on the overall content of the present specification. The terms used herein are only for describing the embodiments, and should not be construed as limitative. Unless the context clearly indicates otherwise, the singular forms are intended to include the plural forms as well. It should be understood that the terms "comprises," "comprising," "includes," and "including," when used herein, specify the presence of stated features, numerals, steps, operations, elements, or combinations thereof, but do not preclude the presence or addition of one or more other features, numerals, steps, operations, elements, or combinations thereof. Also, terms such as "unit", "device", "module", "block", and the like described in the specification refer to units for processing at least one function or operation, which may be implemented by hardware, software, or a combination of hardware and software.

Figure 1:
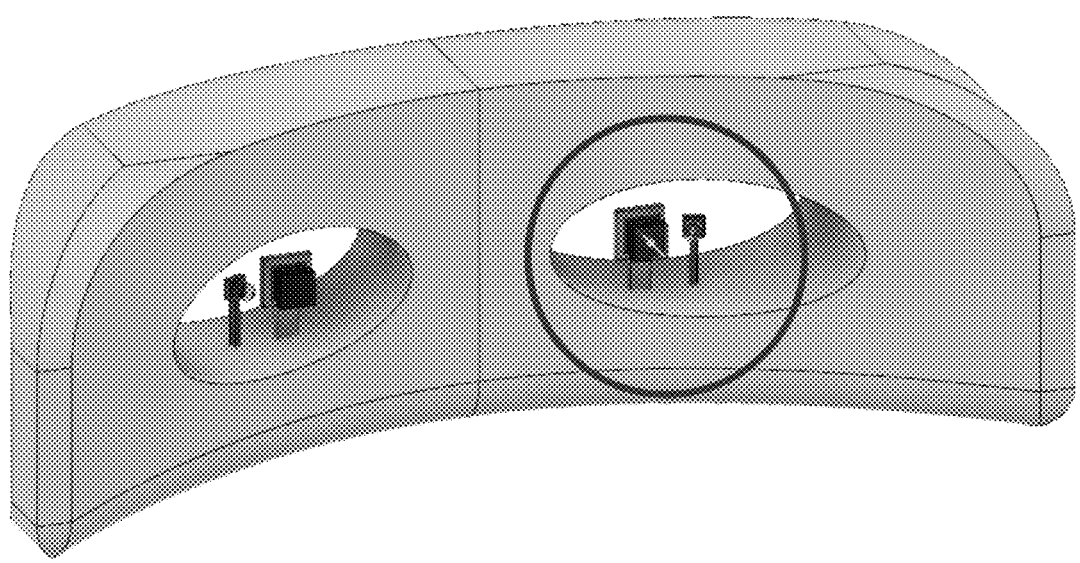
FIG. 1 shows an implementation example of an apparatus for measuring eye movement according to an embodiment of the present disclosure.
Figure 2:
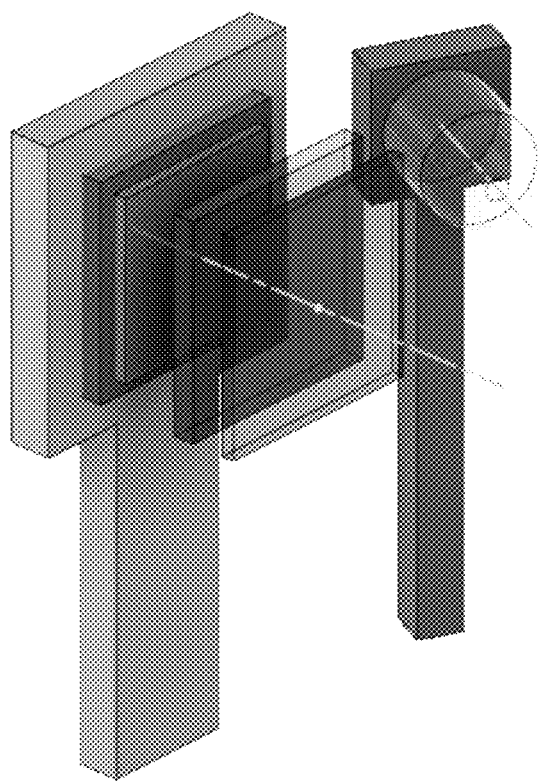
FIG. 2 shows an enlarged view of the camera module in the apparatus for measuring eye movement of FIG. 1.
Figure 3:
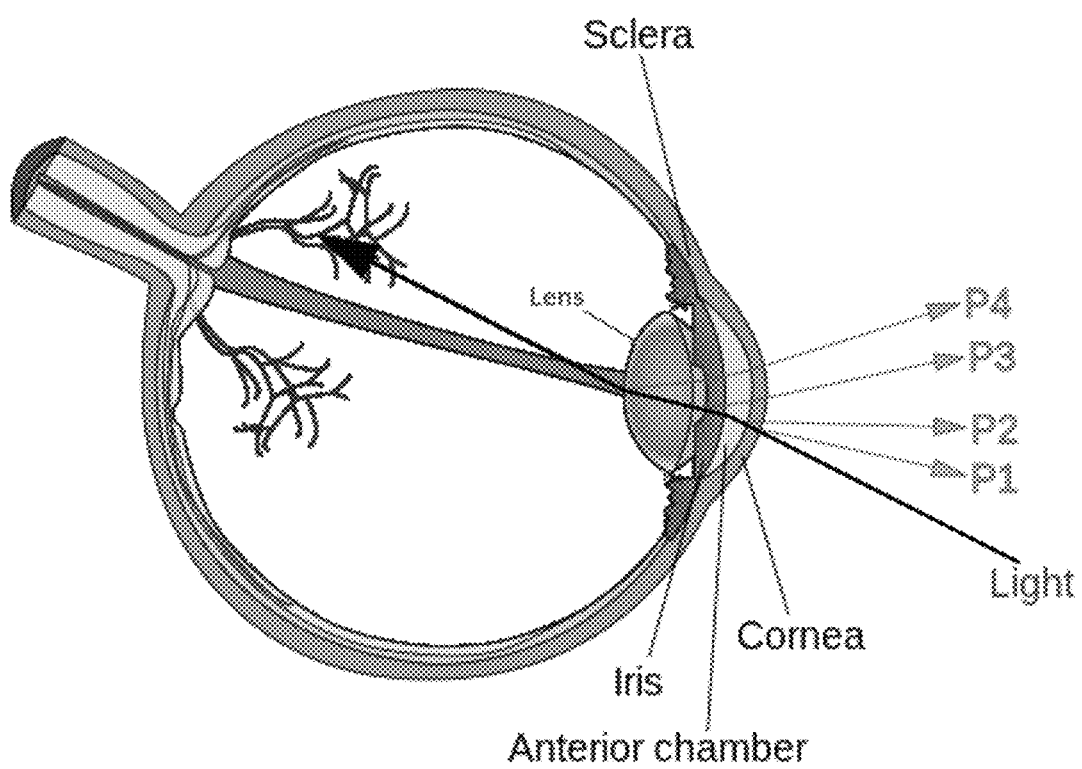
FIG. 3 is a diagram for explaining the Purkinje reflection for eye movement tracking.

FIG. 1 shows an implementation example of an apparatus for measuring eye movement according to an embodiment of the present disclosure, FIG. 2 shows an enlarged view of the camera module in the apparatus for measuring eye movement of FIG. 1, and FIG. 3 is a diagram for explaining the Purkinje reflection for eye movement tracking.

As shown in FIG. 1, the apparatus for measuring eye movement of this embodiment may be implemented in the form of the most general-purpose goggles, for example. Here, the goggles are a wearable device that allows a camera module for substantially measuring eye movement to be placed at a designated location around the eye of a person to be measured. The apparatus for measuring eye movement may be implemented in various forms other than goggles, but the goggle type is mainly used because it minimizes the influence of the surrounding environment, has fewer restrictions on the movement of the person to be measured, and makes measurement easier. Therefore, it is assumed here that the apparatus for measuring eye movement is implemented in the form of goggles.

In addition, a display may be placed in front of the field of view of a person to be measured. Here, the display may display a target for measuring eye movement. For example, the display may display a target as a white dot on a black background or in various pre-designated patterns, and the target may be provided in various ways, such as being fixed at a specific location or moving along a designated path. Here, the display may be implemented within the goggles like an existing VR device, but may also be implemented as a separate display device provided outside the goggles.

In addition, in the apparatus for measuring eye movement, camera modules for detecting eye movements of the person to be measured are placed at the positions of both eyes of the person to be measured. In particular, in this embodiment, the camera modules do not directly capture eye images to measure eye movement. The camera module may be configured to include a light source and a camera sensor, as shown in FIG. 2, to precisely detect minute movements of the eye. The light source emits light toward the eye, and the camera sensor detects the reflected light emitted from the light source and reflected from the eye.

When a camera module attempts to observe eye movement by photographing the entire eye, not only does it require a lot of computation, but it is also very difficult to detect fine eye movement because it appears as a very small amount of change in the entire eye image. However, when a tiny point light source is emitted to the eye and the camera sensor detects the light reflected from the eye, the position of the reflected light changes significantly even with the slightest movement of the eye, so it is not only easy to check the movement of the eye, and since it is a method that detects only the position of light, it has the advantage of requiring very little computation. In other words, eye movements can be tracked accurately at high speed.

As shown in FIG. 3, for a point light source, reflection from the eye can occur on the surface and back of the cornea, and on the surface and back of the lens, respectively. Because of this, four reflected lights can be incident on the camera sensor in the form of point light sources. This is known as a Purkinje image, and four reflected lights (P1 to P4) can be formed at different positions of the camera sensor, as shown in FIG. 3, depending on the difference in reflected positions from the eye.

Accordingly, the apparatus for measuring eye movement can accurately measure eye movement by detecting changes in the position of reflected light detected by the camera sensor. Here, the apparatus for measuring eye movement may also measure eye movement by detecting all four reflected lights (P1 to P4), but detecting all four reflected lights (P1 to P4) not only reduces efficiency, but can also cause misdetection of eye movements by misidentifying different reflected lights. However, as shown in FIG. 3, the four reflected lights (P1 to P4) reflect light at different angles, so the position of the camera sensor relative to the direction in which the light source emits light can be adjusted so that only at least one of the four reflected lights (P1 to P4) enters the camera sensor. In this case, the position of the camera sensor may be adjusted so that only the brightest reflected light (P1) from the corneal surface among the four reflected lights (P1 to P4) is detected.

Figure 4:
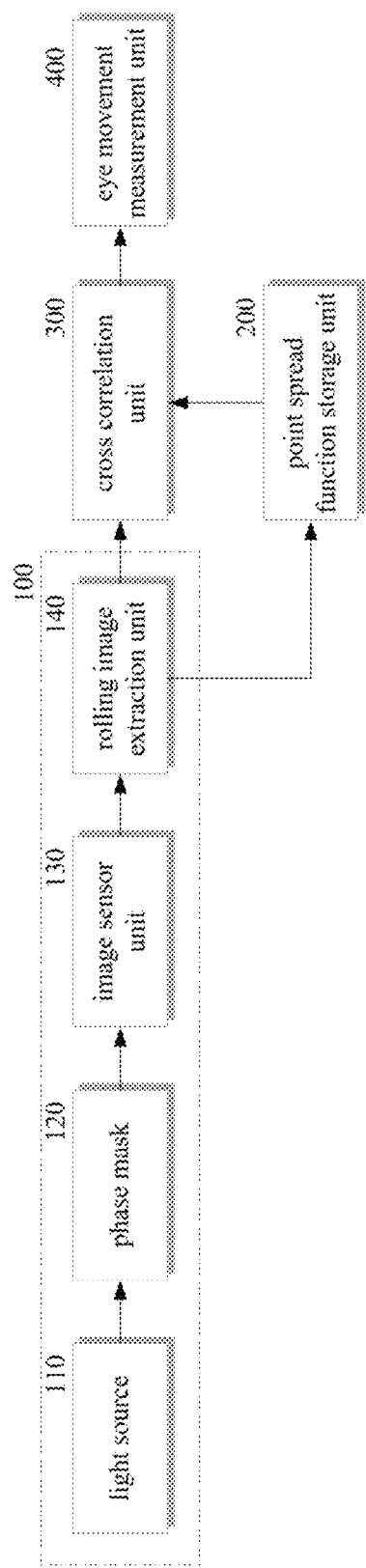
FIG. 4 shows a schematic configuration of the apparatus for measuring eye movement according to an embodiment of the present disclosure.
Figure 5:
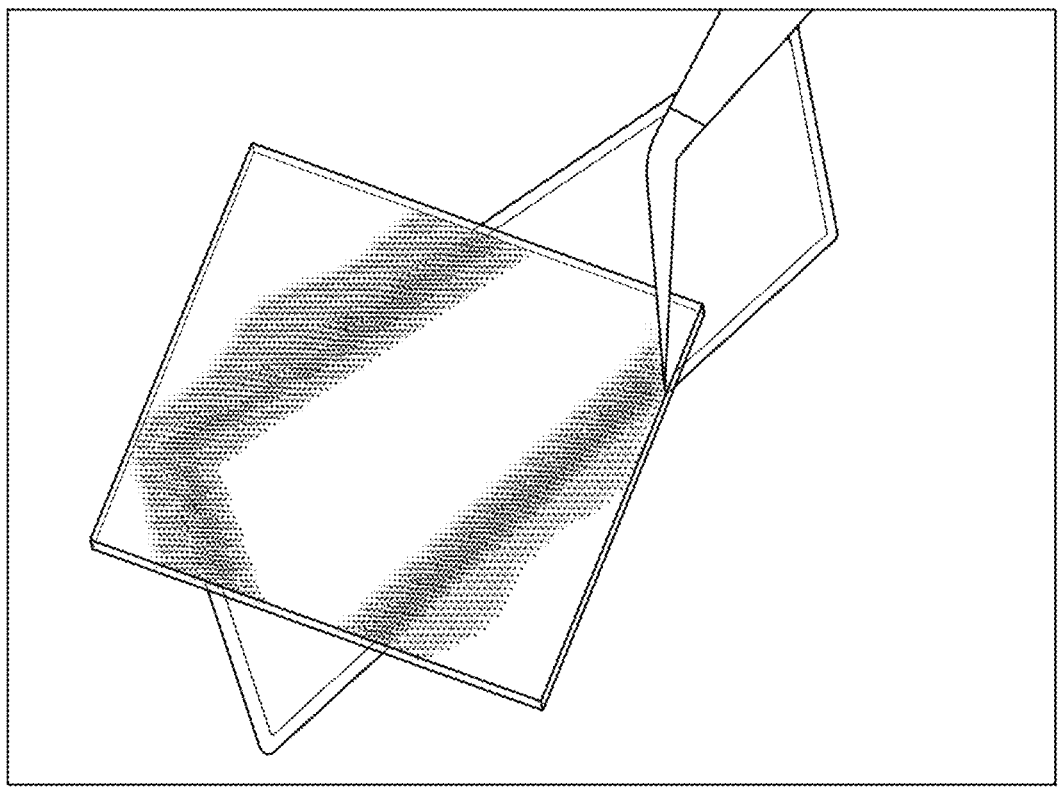
FIG. 5 shows an actual implementation example of the phase mask of FIG. 4.
Figure 6:
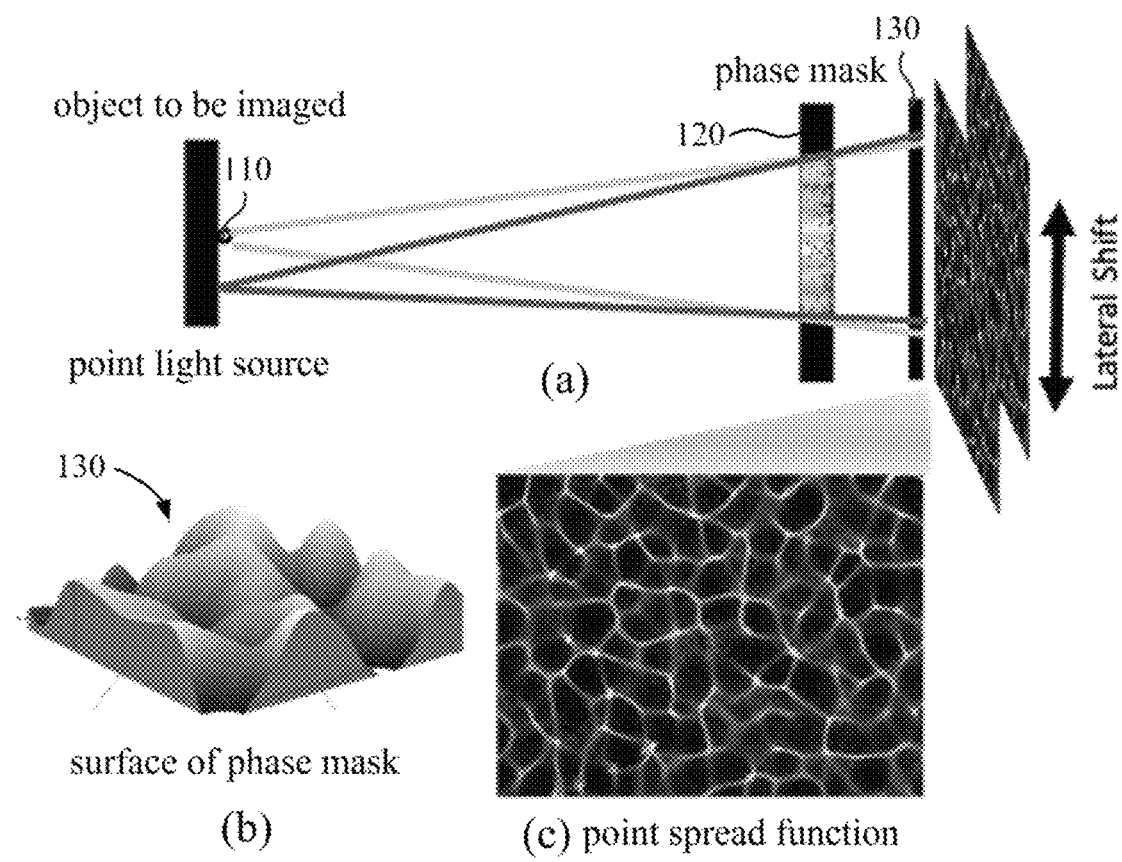
FIG. 6 is a diagram for explaining the concept of a phase mask-based lens-less imaging method.
Figure 7A:
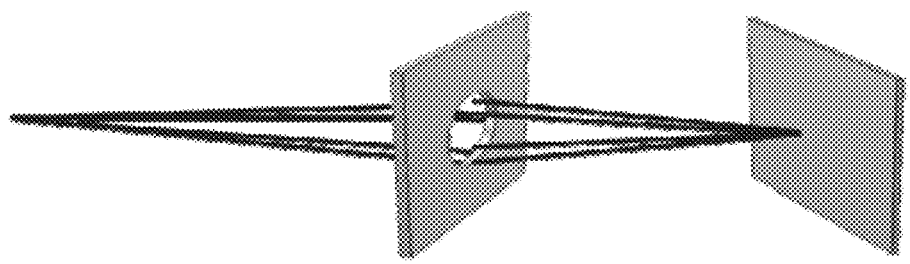
FIGS. 7A and 7B are diagrams for explaining the operations of the lens-based imaging method and the phase mask-based lens-less imaging method.
Figure 7B:
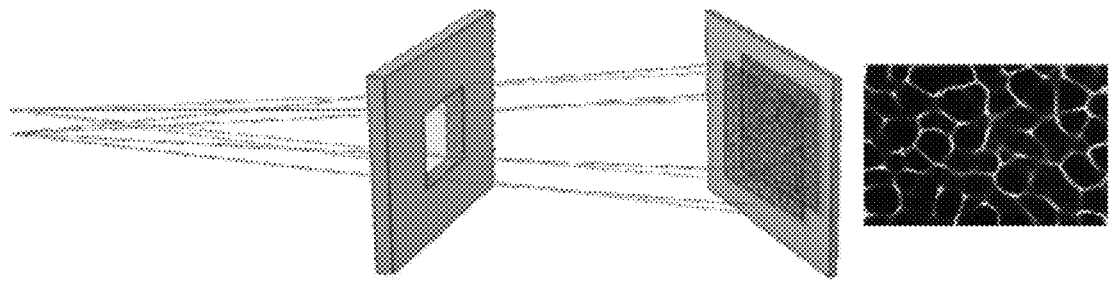
Figure 8:
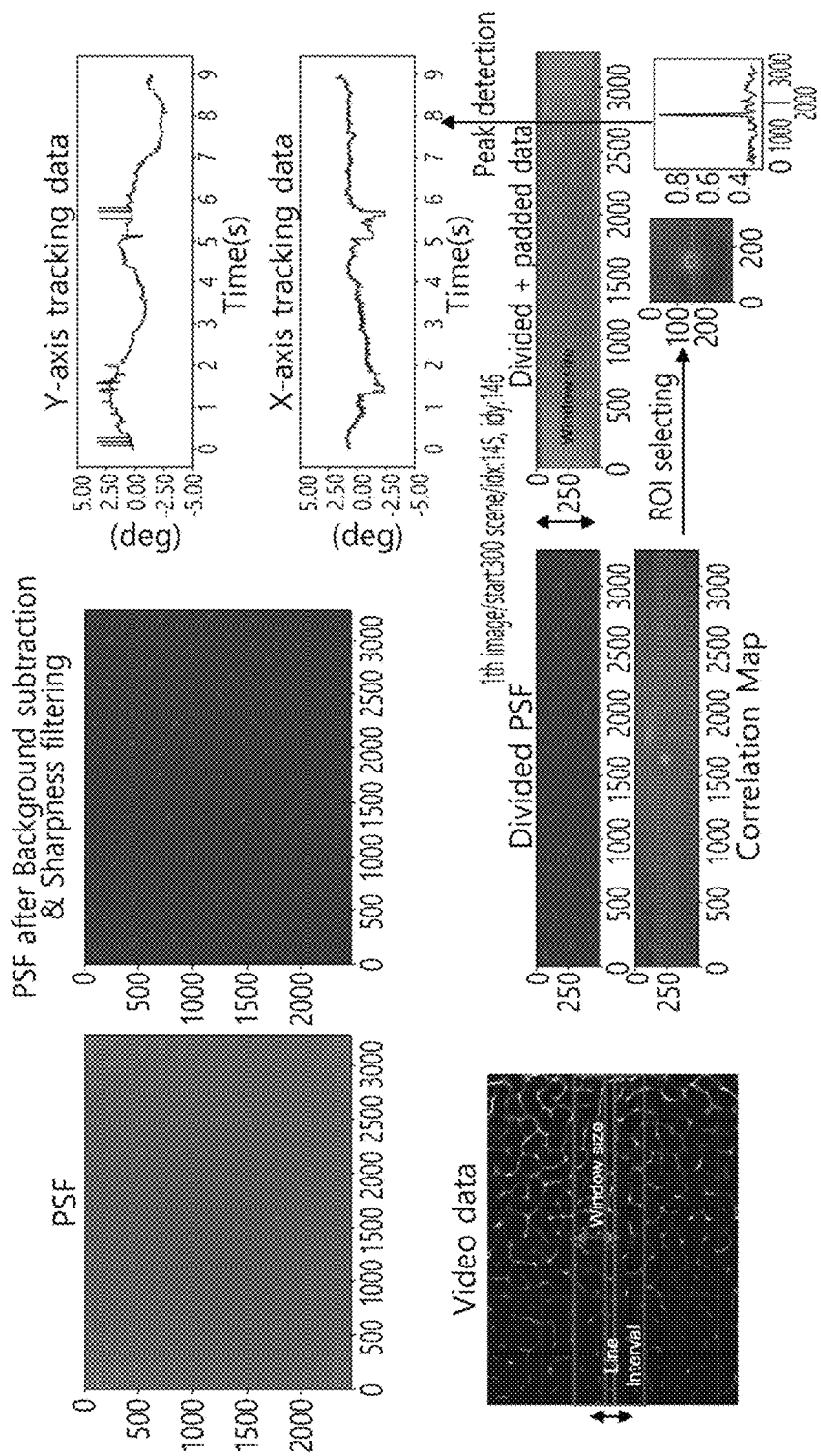
FIG. 8 is a diagram for explaining a method for measuring eye movement based on an image acquired using a lens-less imaging method.

FIG. 4 shows a schematic configuration of the apparatus for measuring eye movement according to this embodiment, FIG. 5 shows an actual implementation example of the phase mask of FIG. 4, and FIG. 6 is a diagram for explaining the concept of a phase mask-based lens-less imaging method. In addition, FIGS. 7A and 7B are diagrams for explaining the operations of the lens-based imaging method and the phase mask-based lens-less imaging method, and FIG. 8 is a diagram for explaining a method for measuring eye movement based on an image acquired using a lens-less imaging method.

Referring to FIG. 4, the apparatus for measuring eye movement according to this embodiment may include an image acquisition unit 100, a point spread function storage unit 200, a cross correlation unit 300, and an eye movement measurement unit 400.

As shown in FIGS. 1 and 2, the image acquisition unit 100 is placed in front of the eye of a person to be measured, emits light in the direction of the eye, and acquires a reflection image by detecting reflected light reflected from the eye. Here, the image acquisition unit 100 of this embodiment acquires a phase-converted image, unlike a typical lens camera module.

In this embodiment, the image acquisition unit 100 may include a light source 110, a phase mask 120, an image sensor unit 130, and a rolling image extraction unit 140. The light source 110 may be a point light source that emits in the direction of the eye, as shown in FIGS. 1 and 2, and may be implemented with an IR LED, for example.

The phase mask 120 is located in front of the image sensor unit 130 and converts the phase of reflected light that is reflected from the eye and incident. The phase mask 120 is a component that replaces the lens provided in a general camera module.

Here, as shown in FIG. 5, the phase mask 120 may be using a transparent film, etc., as a transparent material that allows light to pass through, and as shown in (b) of FIG. 6, one surface of the phase mask 120 is formed to have different heights at each position according to an irregularly shaped phase shift pattern. That is, the phase mask 120 has various patterns of different sizes, heights, and shapes formed on one surface, and diffuses and refracts light at different refractive indices for each position, thereby converting it to a pattern similar to a wave pattern as shown in (c) of FIG. 6 and FIG. 7B. In this embodiment, a pattern that changes the phase of incident light by having different heights for each position is called a phase shift pattern. Here, the height on one surface of the phase mask 120 is shown as a pattern that changes in the form of a continuous curve, but in some cases, it may be implemented as a pattern that changes discontinuously.

In addition, when the angle at which light is incident on the phase mask 120 at a fixed position, that is, the position of the light changes, as shown at the right end of (c) of FIG. 6 and FIG. 7B, the entire pattern projected on the image sensor unit 130 is shifted in the lateral direction corresponding to the change in position of light.

As such, when using the phase mask 120, the entire pattern projected on the image sensor unit 130 is shifted according to a change in the position of light, so even if only the position where some areas in the entire pattern moved is accurately detected, the position where the entire pattern moved is also the same. Accordingly, the position of light can be accurately detected even if only the movement of a partial area of the pattern is confirmed. That is, in this embodiment, the reason why the image acquisition unit 100 uses the phase mask 120 instead of the lens is to accurately determine the location where light reflected from the eye is incident even when only a partial range is acquired from the image acquired through the image sensor unit 130.

The image sensor unit 130 detects light phase-converted through the phase mask 120 and generates a detection signal corresponding to the intensity of the light. The image sensor unit 130 is composed of a plurality of light sensors each corresponding to a plurality of pixels of the image to detect light, and each light sensor generates a detection signal with a size corresponding to the intensity of the incident light.

The rolling image extraction unit 140 acquires an image corresponding to light incident on the camera sensor based on the detection signal generated by the image sensor unit 130. Here, the rolling image extraction unit 140 of this embodiment may acquire images using a rolling shutter method, which sequentially receives detection signals from optical sensors included in a pre-designated size unit among a plurality of optical sensors, rather than a global shutter method that receives detection signals from all optical sensors of the image sensor unit 130 at once.

In the global shutter method, all optical sensors of the image sensor unit 130 are exposed for the same time, and the rolling image extraction unit 140 simultaneously receives detection signals generated during the exposure time to acquire a frame image at a specific point in time. Accordingly, once one frame image is acquired, light must be incident on all optical sensors again during the next exposure time. Therefore, the frame rate is very limited.

On the other hand, in the rolling shutter method, as shown in (a) of FIG. 8, partial images corresponding to a pre-designated window size are sequentially and alternately acquired from the entire frame. That is, in the rolling shutter method, while the detection signal generated from the previously exposed portion of the optical sensor is applied to the rolling image extraction unit 140, the remaining optical sensors may continue to be exposed. In this rolling shutter method, since detection signals are not received from all optical sensors at the same time, only partial images for a certain range can be acquired at a specific time, but partial images for the next range can be acquired very quickly. Although, when using the rolling shutter method, distortion may occur due to differences in when each partial image is acquired as partial images are acquired at different times for each position in the frame, but since partial images are acquired at very short time intervals compared to the global shutter method, temporal resolution can be greatly improved. In other words, the frame rate can be increased.

The rolling image extraction unit 140 may acquire a partial image by receiving a detection signal from an optical sensor included in a range corresponding to a pre-designated size of the window, as shown in (a) of FIG. 8. Here, the size of the window may be determined according to the frame rate required compared to the size of the image sensor unit 130. For example, when trying to achieve 180 fps by applying the rolling shutter method to the image sensor unit 130 with temporal resolution of 60 fps and an optical sensor of 600×800, the window size may be set to 200×800 to acquire partial images by dividing them into three (180/60=3). That is, 600 pixel lines may be divided into 3 to acquire partial images in units of 200 pixel lines.

In this embodiment, according to the rolling shutter method, there is a problem of acquiring only images for a specific range of the frame at a specific point in time, but as described above, in this embodiment, the phase mask 120 is used in order to overcome this problem, and by using the phase mask 120, a change in the position of light can be accurately detected with only a partial image acquired in a certain range.

While a lens, an image sensor unit 130, and a rolling image extraction unit 140 generally constitute a camera module, but in this embodiment, the phase mask 120 is used instead of the lens, so it can be called a lens-less camera module by integrating the phase mask 120, the image sensor unit 130, and the rolling image extraction unit 140.

Meanwhile, the point spread function storage unit 200 confirms and stores in advance a point spread function (PSF) that represents a characteristic of changing the phase of incident light according to a phase shift pattern formed on a phase mask 120 included in the image acquisition unit 100. The point spread function is a function that represents the light quantity distribution obtained on the imaging surface (here, camera sensor) when a point input passes through an optical system, as shown in (c) of FIG. 6 and (b) of FIG. 8.

In other words, the point spread function is a function that represents the pattern formed on the imaging surface after a point light source emitted from a pre-designated reference position passes through an optical system such as a lens, and is a concept that corresponds to the Fourier transform of the impulse response function of an optical system or the transfer function of an electrical signal transmission system.

In the case of a general camera module equipped with a convex lens, after the light passes through the lens, the light is again focused on the camera sensor in the form of a point, so the point spread function (PSF) has a pattern as shown in FIG. 7A. However, in the present disclosure, in the case of a lens-less camera module, since the phase mask 120 is used instead of the lens, light is spread at different intensities at each location according to the phase shift pattern of the phase mask 120, resulting in a point spread function (PSF) as shown in (c) of FIG. 6, FIG. 7B, and (b) of FIG. 8. In particular, when the position of the incident light changes, the entire point spread function (PSF) changes in the form of a lateral shift in response to the changed position of the light, as shown at the right end in (a) of FIG. 6. This means that the location information of incident light can be reflected in each of the plurality of light sensors of the image sensor unit 130.

Therefore, when trying to determine the incident location of light emitted from the light source 110 and reflected from the eye in order to observe the movement of the eye, in a method using a conventional lens, the incident location can be determined by searching for the brightest location in the image acquired by the image sensor unit 130, that is, the location where the amount of light is concentrated. On the other hand, in the method using the phase mask 120, the incident light is converted by the phase mask 120 and spread at different intensities throughout the entire area of the image sensor unit 130, so even if searching for the location with the highest amount of light, the incidence location of light cannot be determined. Therefore, in order to determine the position of the light incident on the phase mask 120, it is necessary to check the shifted position of the point spread function pattern acquired by the currently incident light compared to the point spread function (PSF) corresponding to the phase mask 120 by the light emitted from the pre-designated reference position. Accordingly, the point spread function storage unit 200 acquires and stores in advance a point spread function (PSF) corresponding to the phase mask 120 provided in the image acquisition unit 100.

The point spread function storage unit 200 may simply use the phase-converted image acquired through the phase mask 120 for the point light source at the reference position as a point spread function (PSF), but may also acquire a point spread function (PSF) by previously performing processes such as background subtraction and sharpness filtering, as shown in (c) of FIG. 8, so that the peak of the correlation value can be derived more clearly when the cross-correlation unit 300, which will be described later, cross-correlates with the image acquired by the image acquisition unit 100.

In addition, the point spread function storage unit 200 transmits the stored point spread function (PSF) to the cross-correlation unit 300. Here, the point spread function storage unit 200 may transmit the entire stored point spread function (PSF) to the cross-correlation unit 300, but as shown in (b) of FIG. 8, may also extract a partial point spread function corresponding to the position and size of the window set in the rolling image extraction unit 140 and transmit it to the cross-correlation unit 300. This is to reduce the amount of computation, by extracting and transmitting a partial point spread function in a range corresponding to the partial image acquired according to the rolling shutter method by the rolling image extraction unit 140 from the point spread function (PSF) stored in the point spread function storage unit 200.

However, the point spread function storage unit 200 may extract a partial point spread function with a size larger than the partial image at a position corresponding to the position of the window used by the rolling image extraction unit 140 among the point spread function (PSF), and in this case, the size of the partial point spread function may be set to have a size that includes the movement range in the Y-axis direction of the incident light according to the movement of the eye, which can move during the time period according to the frame rate. This is to enable the cross-correlation unit 300, which will be described later, to acquire accurate correlation values even at the edge of the window, when calculating the correlation value for each position while shifting the partial image on the partial point spread function. In addition, this is to prevent the change in the position of the light from exceeding the size of the point spread window, when observing a change in the position of light by cross-correlating the partial image and the partial point spread function.

The cross-correlation unit 300 cross-correlates the partial image acquired by the rolling image extraction unit 140 and the point spread function (or partial point spread function) transmitted from the point spread function storage unit 200. The cross-correlation unit 300 may perform cross-correlation while moving the position of the partial image with respect to the point spread function (or partial point spread function).

However, the cross-correlation unit 300 may also extract a patch of a pre-designated size from a partial image, and cross-correlate the extracted patch with a point spread function (or partial point spread function). Alternatively, as shown in (e) of FIG. 8, the outer area of the point spread function (or partial point spread function) may be expanded by performing mean replacement padding, and then cross-correlated with the partial image. This is to prevent the correlation value for each location of the point spread function (or partial point spread function) from being significantly lowered due to the size of the partial image and the point spread function (or partial point spread function).

In this embodiment, a lens-less camera module equipped with a phase mask 120 instead of a lens is used, so the light incident on the phase mask 120 is not only distributed and incident on a plurality of optical sensors of the image sensor unit 130 by the phase mask 120, but also the pattern incident on the image sensor unit 130 is shifted as the position of the light changes. This means that the position information of the incident light can be determined using only some optical sensors of the image sensor unit 130. Therefore, even if the rolling image extraction unit 140 acquires only a partial image using the rolling shutter method, the acquired partial image contains the positional information of the incident light, and therefore, when cross-correlated with a point spread function, even with only a partial image, a very high correlation value is derived when the acquired partial image is located in the corresponding region of the point spread function due to a change in the position of light. That is, as in the correlation map shown in (f) of FIG. 8, the correlation value appears very large at the position of the point spread function where the partial image corresponds to the location where light was incident.

Accordingly, the eye movement measurement unit 400 may detect a peak as shown in (g) of FIG. 8 by receiving and analyzing the correlation value acquired as a result of cross-correlation from the cross-correlation unit 300, and measure eye movement by determining the position where light is incident in each frame according to the rolling shutter method, based on the position where the peak is detected, and tracking changes in the position of light. Here, as shown in (h) of FIG. 8, the eye movement measurement unit 400 can track changes in the position of incident light by distinguishing between peaks in the X-axis direction and peaks in the Y-axis direction at each time.

Existing apparatus for measuring eye movement are configured to track changes in the position of light reflected and incident from the eye using a lens, and in order to detect a change in the position of incident light, the pixel position with the highest light intensity must be detected in the image for all pixels of the image sensor unit 130. This is because the light passing through the lens is focused on only some of the plurality of optical sensors of the image sensor unit 130 to form an image, as shown in FIG. 7A. Accordingly, the frame rate is fixed.

On the other hand, when using a lens-less camera module including a phase mask 120 instead of a lens, such as the apparatus for measuring eye movement of this embodiment, when light is incident, the light is phase-converted by the phase mask 120 and is distributed and incident on all pixels of the image sensor unit 130, and at this time, light is incident on each of the plurality of pixels at different intensities depending on the position of the incident light and the phase shift pattern formed on the phase mask 120, and incident in a form in which the overall pattern is shifted. In other words, the positional information of incident light is dispersed and distributed across a plurality of pixels. Accordingly, even when a partial image corresponding to a certain area is acquired rather than an image for all pixels, information about the location where light was incident can be accurately extracted.

If, as in a lens-based camera module, the position of light is to be determined by recovering the image from the image phase-converted by the phase mask 120, the inverse function must be obtained based on the point spread function (PSF) according to the phase shift pattern. In order to obtain the same image as a lens-based image from a phase-converted image, a convolution operation must be performed on the phase-converted image and a point spread function (PSF), and then a deconvolution operation must be performed again. However, in order to perform deconvolution, the inverse matrix for the convolution operator must be obtained, and here, the convolution operator is non-singular, and the detection area is limited by the optical sensor of the image sensor unit 130, so the complexity is so high that the deconvolution operation cannot be performed using a typical method. Because of this problem, when trying to restore an image, an optimization method is generally used that sets up an image conversion model that converts a phase-converted image into a lens-based image, and repeatedly updates the image conversion model so that the error between the image converted from the image conversion model and the lens-based image is minimized. However, this method of using an image conversion model requires repeated computations for optimization every time, so there is a limitation in that it cannot be applied to systems that require fast processing in real time, such as eye movement tracking.

However, when measuring eye movement as in this embodiment, only the position of the light reflected and incident from the eye needs to be confirmed, so there is no need to restore the image for the light. Therefore, it is possible to accurately determine the location where the light was incident just by simply cross-correlating the point spread function (PSF) corresponding to the phase mask 120 and the phase-converted image, and checking the location where the correlation value appears the largest and the location where the peak is detected because the point spread function (PSF) is most similar to the phase-converted image with a pattern in which the point spread function (PSF) is shifted. In addition, even when a partial image corresponding to a certain area is obtained rather than an image for all pixels, information about the location where light was incident can be extracted, so the rolling shutter method can be used, significantly improving temporal resolution.

Here, the apparatus for measuring eye movement has been described assuming that the image acquisition unit 100, the point spread function storage unit 200, the cross-correlation unit 300, and the eye movement measurement unit 400 are configured as a single device, but in some cases, the point spread function storage unit 200, the cross-correlation unit 300, and the eye movement measurement unit 400 may be implemented in an external server, and the apparatus for measuring eye movement may include an image acquisition unit 100 and a communication unit (not shown) that transmits the acquired partial image to a server.

Figure 9:
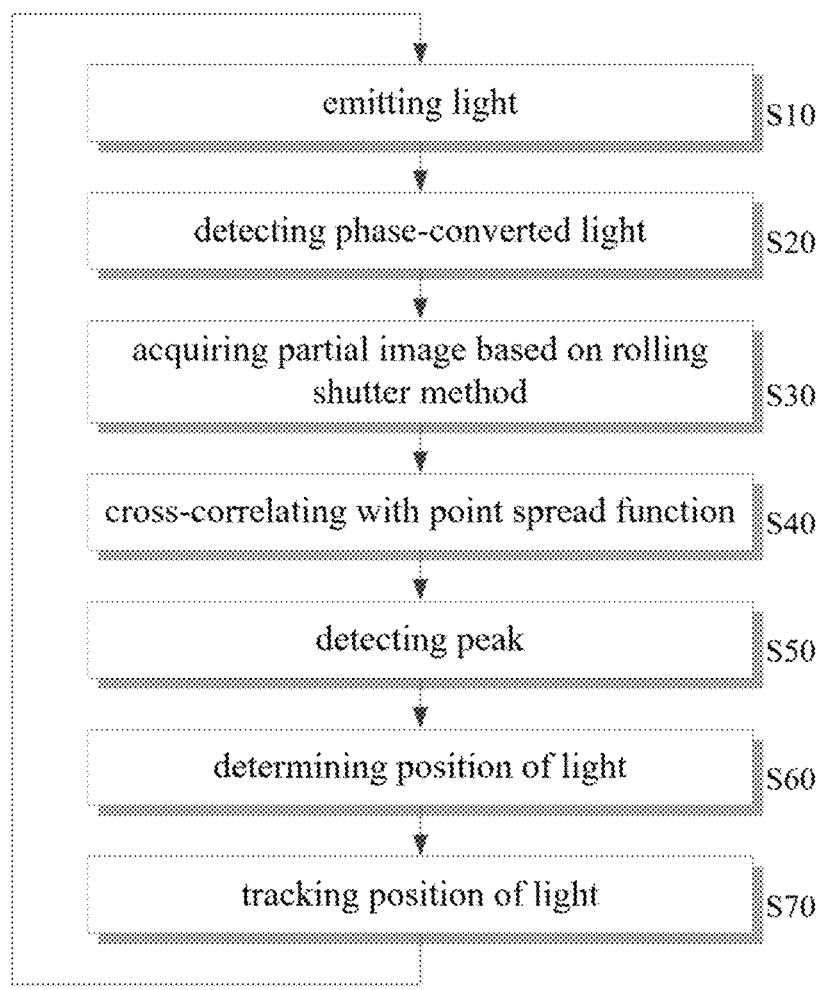
FIG. 9 shows a method for measuring eye movement according to an embodiment of the present disclosure.

FIG. 9 shows a method for measuring eye movement according to an embodiment of the present disclosure.

Referring to FIGS. 1 to 8, FIG. 9 is described as follows. In the method for measuring eye movement according to this embodiment, first, the light source 110 emits light in the direction of the eye (S10). Then, the light that is reflected from the eye, passes through the phase mask 120 implemented as a transparent film formed to have different heights at each position according to an irregularly shaped phase shift pattern on one surface, and is incident on the image sensor unit 130 is detected (S20).

According to the rolling shutter method, a partial image is acquired based on detection signals generated from optical sensors within a range designated by a window of a pre-designated size among the plurality of optical sensors of the image sensor unit 130 (S30). Here, once the partial image is acquired, the position of the window may be changed to sequentially and alternately select a plurality of optical sensors of the image sensor unit 130.

Meanwhile, once the partial image is acquired, the acquired partial image is cross-correlated with a point spread function (PSF) obtained in advance corresponding to the phase shift pattern of the phase mask 120 (S40). This is because since the phase conversion image acquired from the image sensor unit 130 appears in a shifted form of the point spread function (PSF) acquired by incident light onto the phase mask 120 at a pre-designated position, depending on the angle of the incident light, that is, the location, when cross-correlating the partial image and the point spread function (PSF), the correlation value appears very high at the position corresponding to the incident angle of light.

Accordingly, once the correlation value for each position of the partial image is derived as a result of the cross-correlation, a peak in which the correlation value appears significantly higher at a specific location than at other locations is detected (S50). Then, based on the position of the partial image where the peak was detected, the position, that is, the angle, at which the light was incident is determined (S60). Then, the position of the light is tracked by checking the change in the currently determined position of the light compared to the previously determined position of the light, and the eye movement is measured based on the change in the light position accumulated and tracked over time (S70).

A method according to an embodiment of the disclosure can be implemented as a computer program stored in a medium for execution on a computer. Here, the computer-readable medium can be an arbitrary medium available for access by a computer, where examples can include all types of computer storage media. Examples of a computer storage medium can include volatile and non-volatile, detachable and non-detachable media implemented based on an arbitrary method or technology for storing information such as computer-readable instructions, data structures, program modules, or other data, and can include ROM (read-only memory), RAM (random access memory), CD-ROM's, DVD-ROM's, magnetic tapes, floppy disks, optical data storage devices, etc.

While the present disclosure is described with reference to embodiments illustrated in the drawings, these are provided as examples only, and the person having ordinary skill in the art would understand that many variations and other equivalent embodiments can be derived from the embodiments described herein.

Therefore, the true technical scope of the present invention is to be defined by the technical spirit set forth in the appended scope of claims.

What is claimed is:

1. An apparatus for measuring eye movement comprising:
   a light source that emits light in the direction of an eye;
   a phase mask that phase-converts light reflected and incident from the eye according to a pre-formed phase shift pattern;
   an image sensor unit including a plurality of optical sensors that generate a plurality of detection signals by detecting light that is phase-converted by the phase mask and distributed and projected at different intensities for each position;
   a rolling image extraction unit that sequentially moves a window of a pre-designated size for the plurality of optical sensors according to a rolling shutter method and generates a partial image by receiving a detection signal generated at an optical sensor included in the window;
   a point spread function storage unit that pre-stores a point spread function corresponding to the phase shift pattern of the phase mask;
   a cross-correlation unit that cross-correlates the partial image and the point spread function to obtain a correlation value according to the position between the partial image and the point spread function; and
   an eye movement measurement unit that detects the peak of the correlation value, and tracks the position of light by determining and accumulating the angle at which light is incident based on the position between the partial image at the detected peak and the point spread function, thereby analyzing eye movement.

2. The apparatus for measuring eye movement according to claim 1,
   wherein the phase mask is implemented as a transparent film formed to have different heights at each position on one side according to the phase shift pattern.

3. The apparatus for measuring eye movement according to claim 2,
   wherein the point spread function is obtained in advance based on an image pattern generated by the light emitted from a light source at a pre-designated reference position being phase-converted through the phase mask and then projected onto the image sensor unit.

4. The apparatus for measuring eye movement according to claim 3, wherein the point spread function is obtained by background subtraction and sharpness filtering on the image pattern generated by the projection.

5. The apparatus for measuring eye movement according to claim 1,
wherein the window is set to a size that can distinguish the plurality of optical sensors according to a ratio between a frame rate according to a time interval required for optical position tracking compared to a frame rate designated for the image sensor unit.

6. The apparatus for measuring eye movement according to claim 1,
wherein the cross-correlation unit extracts a partial point spread function of a size corresponding to the window at a position corresponding to the partial image from the point spread function, and cross-correlates the partial image and the extracted partial point spread function.

7. The apparatus for measuring eye movement according to claim 6,
wherein the cross-correlation unit expands the outline of the partial point spread function by a pre-designated size, performs mean replacement padding on the expanded area, and then performs cross-correlation.

8. The apparatus for measuring eye movement according to claim 6,
wherein the eye movement measurement unit detects the position where the peak occurs separately in the X-axis direction and the Y-axis direction, and accumulates peak positions detected in each of the X-axis and Y-axis directions, thereby tracking changes in the position of the light.

9. The apparatus for measuring eye movement according to claim 1,
wherein the apparatus for measuring eye movement further comprises:
a goggle-shaped housing in which the light source, the phase mask, the image sensor unit, and the rolling image extraction unit are disposed at a pre-designated position; and
a communication unit transmitting the partial image acquired from the rolling image extraction unit to a server including the cross-correlation unit and the eye movement measurement unit.

10. A method for measuring eye movement performed in an apparatus for measuring eye movement, the method comprising the steps of:
emitting light in the direction of an eye;
detecting the light reflected and incident from the eye being phase-converted through a phase mask in which a pre-designated phase shift pattern is formed in advance, distributed and projected at different intensities for each position, an image sensor unit generating a plurality of detection signals by detecting the light with a plurality of optical sensors;
generating a partial image by sequentially moving a window of a pre-designated size for the plurality of optical sensors according to a rolling shutter method and receiving a detection signal generated at an optical sensor included in the window;
cross-correlating the partial image and a point spread function pre-stored corresponding to the phase shift pattern of the phase mask to obtain a correlation value according to the position between the partial image and the point spread function; and
detecting the peak of the correlation value, tracking the position of light by determining and accumulating the angle at which light is incident based on the position between the partial image at the detected peak and the point spread function, thereby measuring eye movement.

11. The method for measuring eye movement according to claim 10,
wherein the phase mask is implemented as a transparent film formed to have different heights at each position on one side according to the phase shift pattern.

12. The method for measuring eye movement according to claim 11,
wherein the point spread function is obtained in advance based on an image pattern generated by the light emitted from a light source at a pre-designated reference position being phase-converted through the phase mask and then projected onto the image sensor unit.

13. The method for measuring eye movement according to claim 12,
wherein the point spread function is obtained by background subtraction and sharpness filtering on the image pattern generated by the projection.

14. The method for measuring eye movement according to claim 10,
wherein the step of generating a partial image includes the steps of:
setting the window to a size that can distinguish the plurality of optical sensors according to a ratio between a frame rate according to a time interval required for optical position tracking compared to a frame rate designated for the image sensor unit; and
acquiring the partial image by receiving detection signals generated from optical sensors included in the window, while sequentially alternating the positions of the windows of the set size for the plurality of optical sensors.

15. The method for measuring eye movement according to claim 10,
wherein the step of obtaining a correlation value includes the steps of:
extracting a partial point spread function of a size corresponding to the window at a position corresponding to the partial image from the point spread function; and
cross-correlating the partial image and the partial point spread function, thereby obtaining the correlation value.

16. The method for measuring eye movement according to claim 15,
wherein the step of extracting a partial point spread function includes the steps of:
extracting the partial point spread function of a size corresponding to the window; and
expanding the outline of the extracted partial point spread function by a pre-designated size, and performing mean replacement padding on the expanded area.

17. The method for measuring eye movement according to claim 16,
wherein the step of measuring eye movement includes the steps of:
detecting the position where the peak occurs separately in the X-axis direction and the Y-axis direction; and
accumulating peak positions detected in each of the X-axis and Y-axis directions, thereby tracking changes in the position of the light.

* * * * *